United States Patent [19]
Czerniawski

[11] Patent Number: 5,183,414
[45] Date of Patent: Feb. 2, 1993

[54] CANTILEVER DENTAL IMPLANT GUIDESTENT AND METHOD

[76] Inventor: Benjamin J. Czerniawski, 33204 Hampshire, Livonia, Mich. 48154

[21] Appl. No.: 691,713

[22] Filed: Apr. 26, 1991

[51] Int. Cl.$^5$ ............................................. A61C 3/02
[52] U.S. Cl. ................................................... 433/76
[58] Field of Search ............................... 433/76, 75, 6

[56] References Cited

U.S. PATENT DOCUMENTS

| | | | |
|---|---|---|---|
| 2,233,722 | 3/1941 | Weigele | 433/76 |
| 4,251,210 | 2/1981 | Weissman | 433/76 |
| 4,998,881 | 3/1991 | Lauks | 433/75 |
| 5,015,183 | 5/1991 | Fenick | 433/76 |

OTHER PUBLICATIONS

Template for Positioning and Angulation of Intraosseous Implants—David R. Burns, D.M.D., Donald G. Crabtree, D.D.S., Dewey H. Bell, D.D.S.-5 pages.

Practical Mandibular Implantation—D. Wedgwood, B.D.S., M.B., B.S.-5 pages.
Surgical Guidestents for Placement of Implants—Thomas J. Balshi, DDS, FACP, and Don G. Garver, DDS, FACP-3 pages.

*Primary Examiner*—John J. Wilson
*Attorney, Agent, or Firm*—Harness, Dickey & Pierce

[57] ABSTRACT

The present invention is directed to a cantilevered surgical stent for use in dental implant surgery for spacially orienting the implant fixture with respect to a predetermined reference point. The cantilevered surgical stent of the present invention provides the surgeon with enhanced access to the surgical site, the ability to accommodate virtually any direction of flap reflection, and the ability to apically locate sufficient bone volume for primary or secondary surgical sites with respect to the predetermined spacial reference point. As a related object, the present invention is directed to a surgical protocol for dental implant placement procedure using the cantilevered surgical stent.

15 Claims, 5 Drawing Sheets

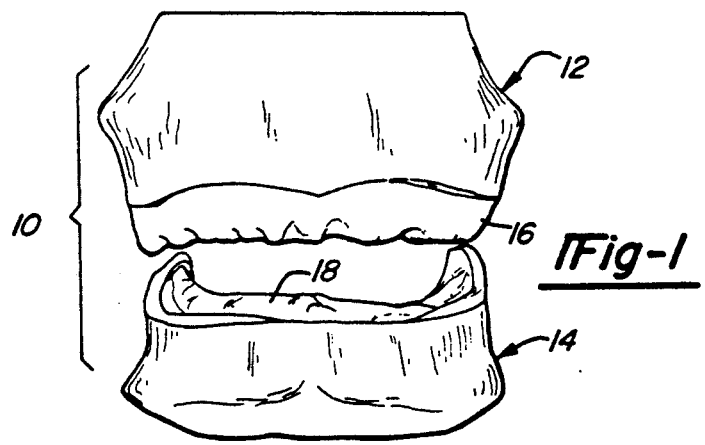
Fig-1
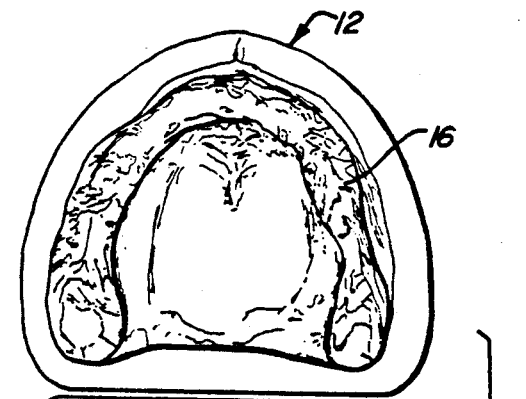
Fig-2
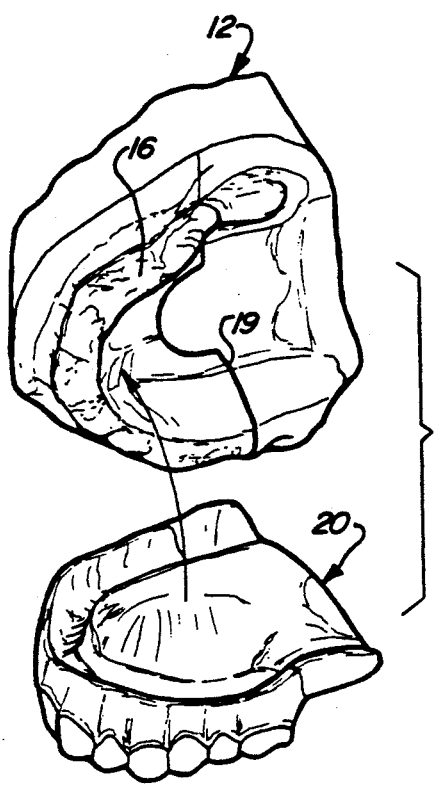
Fig-3A
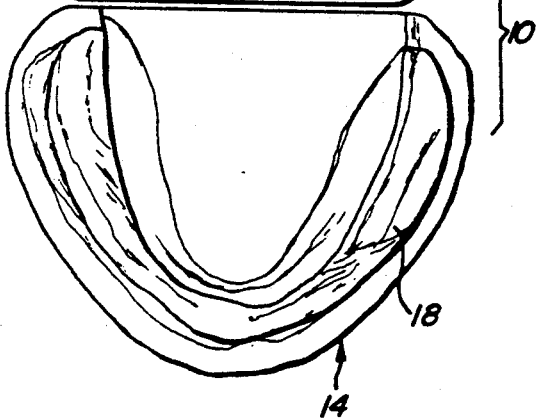

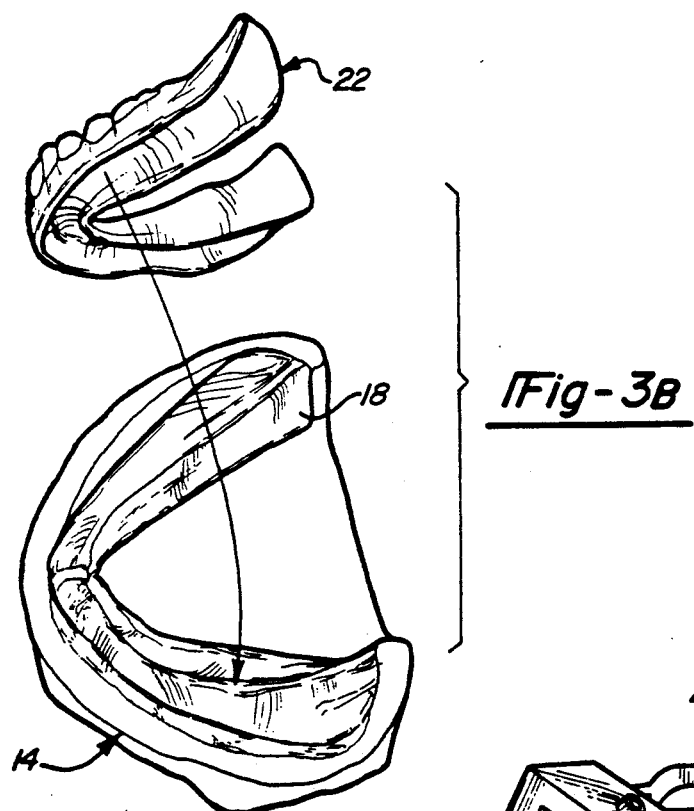
_Fig-3B_
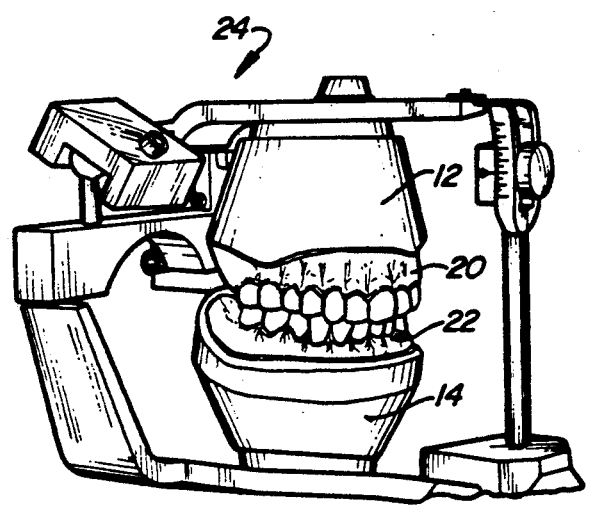
_Fig-4_
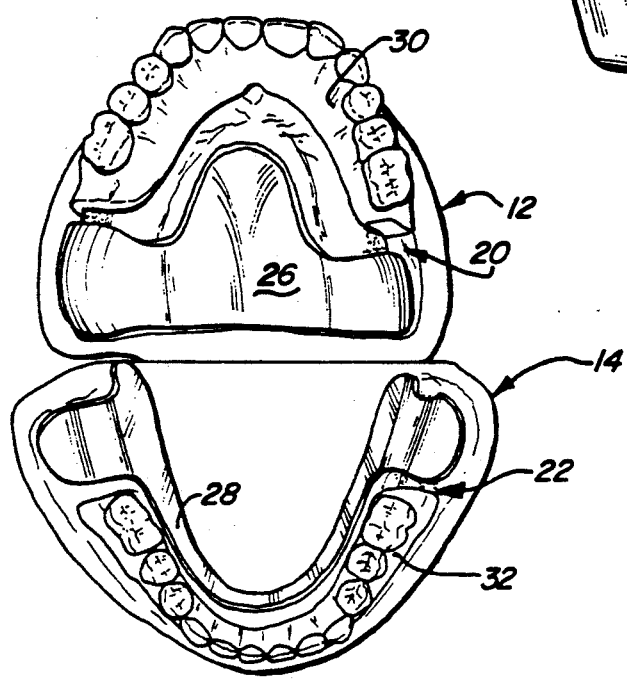
_Fig-5_

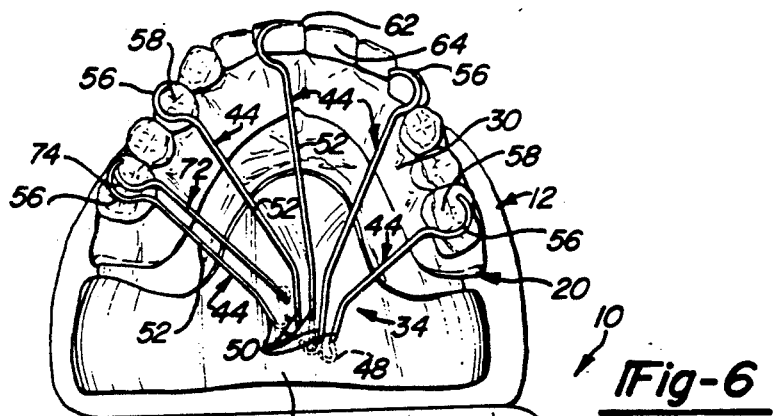
_Fig-6_
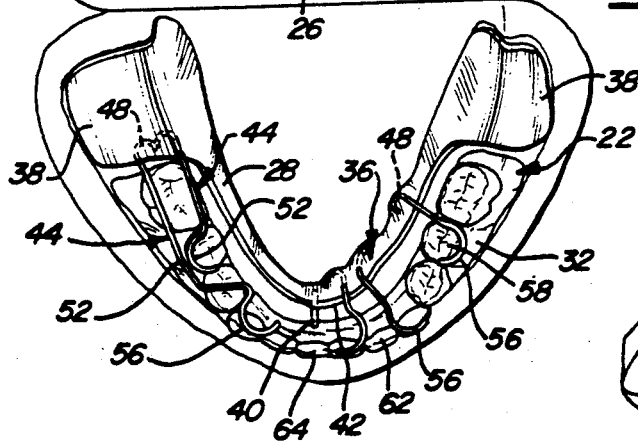
_Fig-7A_
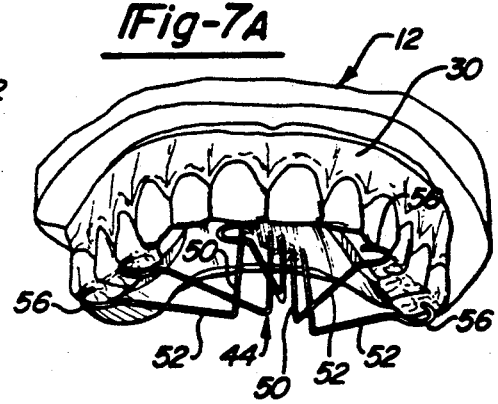
_Fig-7B_
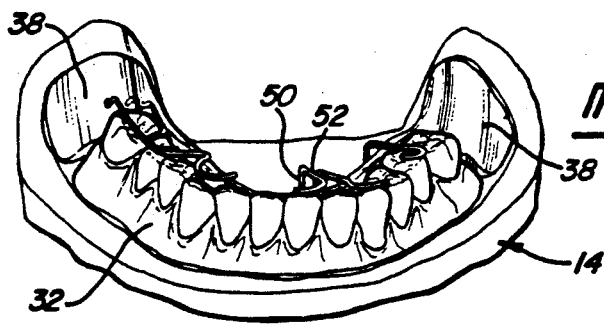
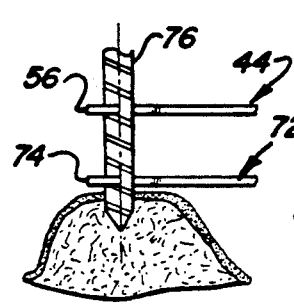
_Fig-10_
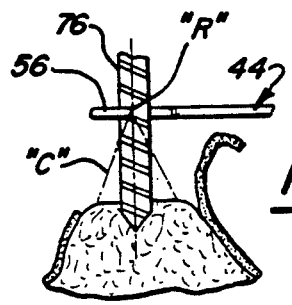
_Fig-11_

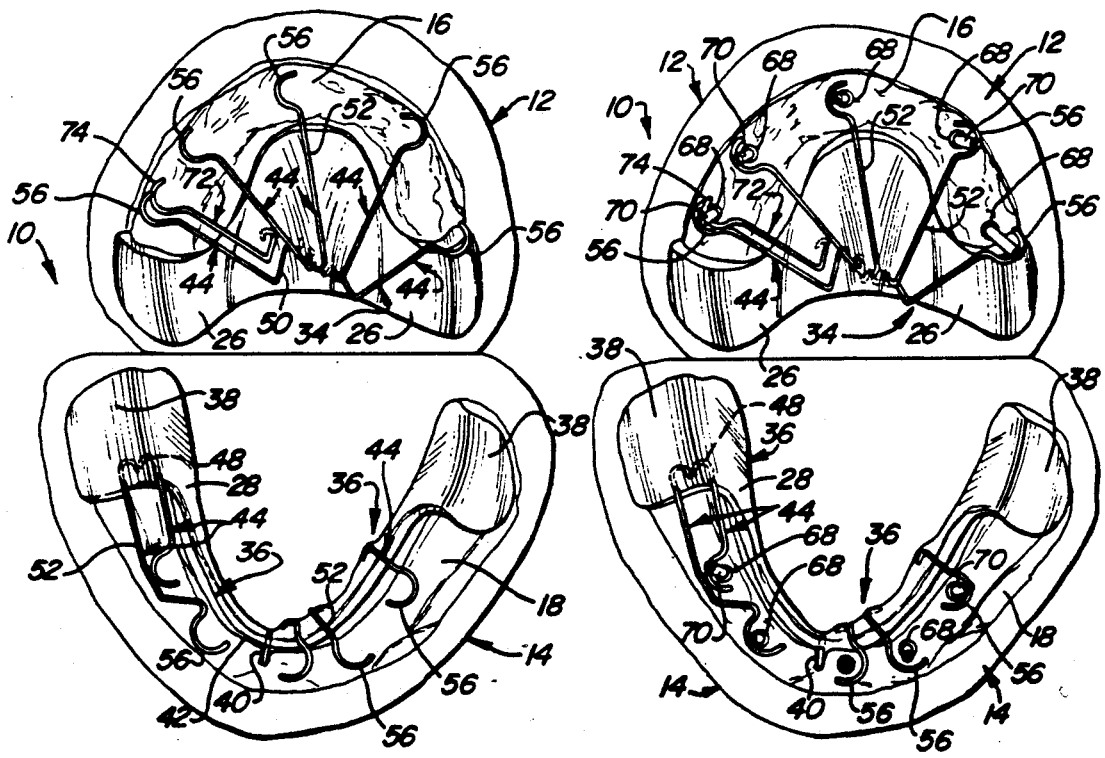
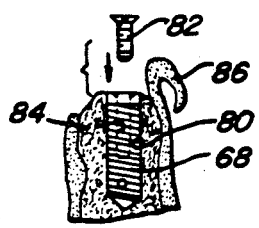
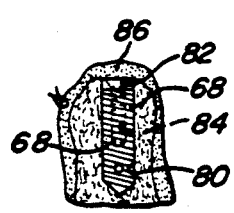
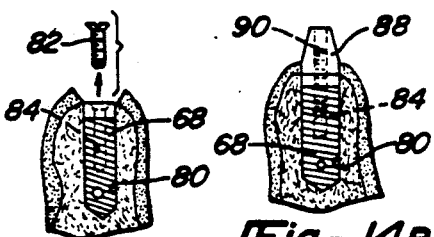
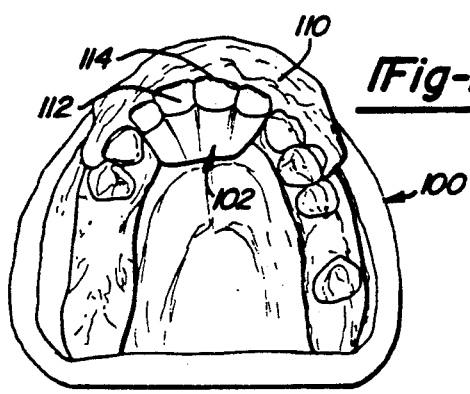
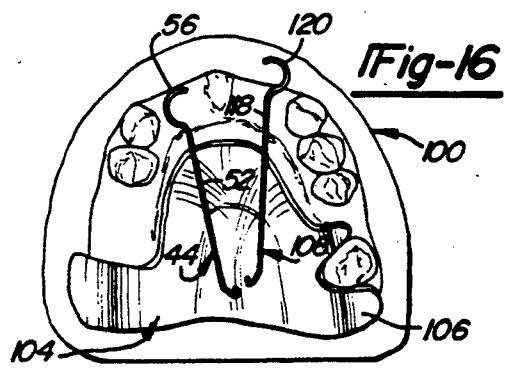

CANTILEVER DENTAL IMPLANT GUIDESTENT AND METHOD

BACKGROUND OF THE INVENTION

The present invention relates generally to dental implants and, more particularly, to a method and apparatus for spatially positioning and angulating implanted fixtures with respect to existing bone tissue.

Various treatments currently exist for patients suffering from partial and full edentulous situations. Modernly, a majority of these edentulous patients are fitted with conventional removable prostheses, such as bridges and dentures. Unfortunately, utilization of a conventional dental prosthesis is often contraindicative for those edentulous patients suffering from insufficient retention, excessive resorption, functional disturbances (i.e. nausea and gagging) and/or unsatisfactory phonetics and esthetics.

As an alternative to wearing conventional dentures, the patient may be a candidate for surgical implantation of tissue integrated (i.e. osseointegrated) fixtures anchored in existing jawbone tissue and upon which a natural-looking prosthesis is retained. When property positioned and angulated, osseointegration of dental implants into vital existing jawbone tissue can provide a predictable prognosis for restoration or reconstruction of the fully or partially edentulous patient.

In most dental implants, an oral surgeon surgically prepares the patient's jaw and a restorative dentist fabricates the prosthetic device. However, prior to surgical implantation, the implant surgeon and the restorative dentist perform a standard clinical examination to evaluate the patient's prognosis for successful tissue integration. This pre-surgical protocol requires great care and precision in the determination of adequate bone volume and quality for satisfactory implant (i.e. fixture) placement so as to increase the prognosis of prosthodontic satisfaction.

In general, protocol for dental implantation includes two surgical procedures for implanting the anchors and attaching the abutments thereto, and the fabrication of the diagnostic and permanent prosthesis by the restorative dentist. Following implantation of the substructural anchors or fixtures, primary (non-angulated) and/or secondary (angulated) abutments are threadably or cementably affixed to the osseointegrated fixtures during the second surgical procedure. Following recuperation, the restorative dentist or prosthodontist fabricates the rigid framework of the permanent prosthesis for attachment to the abutments. Typically, the permanent prosthesis includes teeth or teeth and soft tissue analogues mounted directly to the rigid frame work.

As is known, successful abutment connection and dental prosthesis fabrication are largely dependent on proper placement, spacing and angulation of the implanted fixtures for providing a relatively uniform and functional load distribution and proper occlusal alignment with the opposing teeth or prosthesis. Therefore, surgical templates or stents are generally used by the oval surgeon during fixture implantation surgery for determining the desired "ideal" fixture location with respect to vital bone tissue. Conventional surgical templates or stents are adapted for use (i.e. placement in the patient's mouth) following flap reflection of the soft gingival-mucosal tissue. Such devices generally include one or more small diameter cylindrical guide tubes which are provided to orient and guide each of the various drilling tools (i.e. burs, twist drills and taps) with respect to the underlying bone tissue. The long axis of the cylindrical guide tubes are "angulated" based on results of the diagnostic evaluation and are oriented to direct the drill tools passing therethrough along a predetermined "line-of-action" for drilling the implant bore in a region of adequate bone volume. Unfortunately, conventional templates and stents generally limit the surgeon's direction of flap reflection, impede access and visibility and, most importantly, inhibit the surgeon's ability to controllably variate angulation requirements in view of unanticipated bone trajectory variations.

During implant surgery, it is not uncommon for the surgeon to find the template or stent to be inappropriate after surgical reflection of the soft gum tissue has occurred. When this occurs, the surgeon can either suture the flap and fabricate a new template or continue the surgical procedure using clinical judgement for "free-hand" fixture placement in an effort to approximate fixture location, spacing and angulation with respect to the "ideal" presurgical site. Such free-hand fixture placement generally results in the use of secondary angulated abutments in an effort to eliminate or minimize excessively aberrant implant angulation. Moreover, errors in implanted fixture orientation can easily propagate into potentially unacceptable prosthesis esthetic and functional characteristics. As such, the restorative dentist is faced with the extremely difficult task of fabricating a permanent prosthesis which overcomes the aberrant implant angulation while maintaining the functional and esthetic characteristic of the diagnostic prosthesis previously approved by the patient.

SUMMARY OF THE INVENTION

Accordingly, the present invention is directed to overcoming the disadvantages associated with conventional surgical templates or stents by providing a method and apparatus for spatially orienting the implant fixtures with respect to a predetermined reference point for enhancing the accuracy of the implant fixture positioning, spacing and angulation during the dental implant surgery. In addition, the restorative dentist is able to fabricate a permanent prosthesis based on the predetermined spatial orientation which fulfills all prosthodontic, esthetic and functional needs of the patient.

It is another primary object of the present invention to provide a cantilevered surgical stent adapted to provide the surgeon with enhanced access to the surgical site, the ability to accommodate virtually any direction of flap reflection, and the ability to apically locate sufficient bone volume following soft tissue flap reflection for primary or secondary surgical sites with respect to the predetermined spatial reference point. In a related object, the present invention is directed to a surgical protocol for the dental implant placement procedure using the cantilevered surgical stent.

It is a further object of the present invention to provide a cantilevered surgical stent having one or more cantilevered guide wires that include means for defining the predetermined spatial reference point with respect to the exposed crestal ridge of bone. More specifically, the spatial reference point defines the apex of a conical area extending toward the bone tissue within which the surgeon is allowed to apically look for sufficient bone volume. Furthermore, the cantilevered guide wires can be fabricated to accommodate both primary and secondary surgical sites based on presurgical clinical and diagnostics evaluations for accommodating anticipated variations in available bone trajectory.

Further objects, features and advantages of the present invention will become readily apparent to those skilled in the art from analysis of the following written description, the accompanying drawings and the appended claims.

BRIEF DESCRIPTION OF THE DRAWINGS

FIG. 1 is a front elevational view of maxillary and mandibulary diagnostic casts for a fully edentulous patient;

FIG. 2 is a plan view of the diagnostic casts of FIG. 1;

FIG. 3A is an exploded perspective view of the diagnostic maxillary cast of FIG. 1 and its associated diagnostic prosthesis;

FIG. 3B is an exploded perspective view of the diagnostic mandibulary cast of FIG. 1 and its associated diagnostic prosthesis;

FIG. 4 illustrates the diagnostic casts and prostheses of FIGS. 3A and 3B mounted on an exemplary articulator device;

FIG. 5 is a plan view, similar to FIG. 2, of the diagnostic casts and protheses of FIGS. 3A and 3B with the baseplate portion of each prosthesis severed from its teeth and gum analogue portion;

FIG. 6 is a top plan view, similar to FIG. 5, illustrating maxillary and mandibulary cantilevered surgical stents fabricated in accordance with the teachings of the present invention from the baseplate portions;

FIGS. 7A and 7B are frontal perspective views of the maxillary and mandibulary surgical stents supported from their respective diagnostic casts illustrating the spatial orientation of each guide wire relative to its corresponding diagnostic prosthesis;

FIG. 8 is a top plan view, similar to FIG. 6, with the teeth and gum analogue portions of the diagnostic protheses removed for illustrating placement and spatial orientation of the surgical stents relative to the edentulous ridge crestal surfaces;

FIG. 9 is a view, similar to FIG. 8, showing the trajectory characteristic provided for properly angulating the implanted fixtures using the cantilevered surgical stents;

FIG. 10 schematically illustrates an exemplary drill tool being positioned and angulated by a two-loop guide wire system of the cantilevered surgical stent of the present invention;

FIG. 11 is a single-loop guide wire system associated with the cantilevered surgical stent which provides apical drill trajectory;

FIGS. 12 through 14B schematically illustrates a surgical protocol for the osseointegrated implantation of fixtures and subsequent abutment attachment;

FIG. 15 is a top plan view of a partially edentulous diagnostic cast and its associated diagnostic prosthodontic analogue;

FIG. 16 illustrates the partially edentulous diagnostic cast and diagnostic prosthesis of FIG. 15 with respect to its associated cantilevered surgical stent;

DETAILED DESCRIPTION OF THE INVENTION

Figure 17:
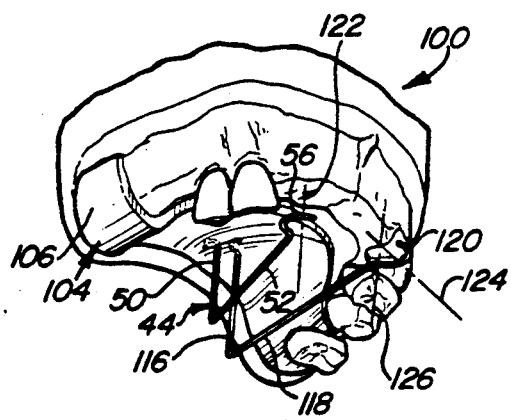
FIG. 17 is a perspective view with the diagnostic prosthesis removed for illustrating spatial placement of cantilevered guide wires adapted to accommodate both primary and secondary surgical sites.

As previously noted, tissue integration or the "osseointegration" of dental implants can provide successful restorative and reconstructive results for the fully or partially edentulous patient. Such dental implants require accurate implant placement within vital bone tissue to satisfy esthetic and functional prosthodontic considerations. Therefore, pre-surgical determination of the positioning, spacing and long axis angulation requirements for the implanted fixtures or anchors must be made to ensure proper occlusal alignment, functional stress distribution and acceptable esthetic results. The implanted fixture must be placed in a vital bone region of the edentulous ridge where the quantity and quality of bone tissue is adequate to provide osseointegrated prosthodontic support.

With this in mind, the present invention is directed to an improvement over currently available surgical guides, templates or stents used by implant surgeons during dental implantation surgery. Accordingly, several exemplary embodiments of cantilevered surgical stents are disclosed which offer the surgeon additional flap reflection considerations, improved visibility, and which permit apical selection of drill trajectory into the bone with respect to a predetermined spatial "reference" point from which the prosthodontist can fabricate a final prosthesis closely approximating the diagnostic prosthesis. Furthermore, the cantilevered surgical stents of the present invention are useful as a diagnostic tool for accommodating both primary and secondary surgical sites while permitting the surgeon and restorative dentist to determine the overall appropriateness of the dental implant proposal based on the clinical examination (i.e. medical history, oral and radiographic examinations, bone sounding, C.T. scans, etc.). The surgeon using all the available information as well as previous clinical experience, diagram anatomy, nervous structures, sinus locations, etc. is able to provide more information to the restorative dentist, for predicting bone availability for implant placement, and thus prosthesis design prior to surgery.

With reference to FIG. 1, a reproduction in artificial stone, or in any other material desired, of a fully edentulous mounted diagnostic casts 10 at appropriate vertical dimension and centric relation is illustrated. Fabrication of a mounted diagnostic casts 10 is a common procedure in the art and any known procedure may be used with the present invention to obtain mounted casts 10. As best seen in FIG. 2, diagnostic casts 10 comprises a maxillary diagnostic cast 12 and a mandibulary diagnostic cast 14 which are accurate replicas that are normally fabricated early in the diagnostic phase by the restorative dentist. As is evident, each of the diagnostic casts is formed to model the patient's maxillary and mandibulary edentulous ridge 16 and 18, respectively, of soft mucosal tissue overlying rigid jawbone tissue.

Diagnostic casts 12 and 14 are submitted to the implant surgeon for his use in predicting bone availability for implant placement based on information gathered from conventional diagnostic testing and experience. The surgeon should detail diagnostic casts 12 and 14 with the highest degree of accuracy such that the restorative dentist can better design the preliminary diagnostic protheses, and thus the cantilevered surgical stents to be described hereinafter. More particularly, as shown in FIG. 3A, the surgeon is to mark (line 19) the most anterior extent of soft tissue which will not be reflected and upon which the cantilevered surgical stents of the present invention will rest during the surgical implant procedure.

Due to the nature of the dental implant procedure associated with the present invention, a duplicate model of maxillary diagnostic cast 12 and mandibulary diagnostic cast 14 are generally made from which the restorative dentist pursues the fabrication of the preliminary or diagnostic (i.e. wax-up) prostheses. As seen in FIGS. 3A and 3B, fully edentulous maxillary and mandibulary analogues 20 and 22, respectively, are shown in association with maxillary and mandibulary diagnostic casts 12 and 14, respectively. Prior art procedures and protocol for the fabrication of diagnostic prostheses 20 and 22 can be used and should include determination of all pertinent information including occlusal relations, patient esthetics, phonetics and functional characteristics. With reference to FIG. 4, diagnostic casts 12 and 14 and their respective protheses 20 and 22 are shown mounted in a articulator device 24 using a centric jaw relation record. As will be appreciated, the preliminary "wax-up" or "try-in" protheses 20 and 22 should meet with patient phonetic and functional approval prior to continuation of any presurgical stent fabrication or permanent prostheses fabrication. As will be better understood hereinafter, fabrication of the cantilevered surgical stents of the present invention are dependent on extremely accurate and approved preliminary diagnostic prostheses.

With reference to FIGS. 5 through 9, a preferred technique for fabrication of cantilevered surgical stents in accordance with the present invention will now be discussed in greater detail. In general, such cantilevered surgical stents provide the surgeon with means for identifying appropriate fixture screw exits locations, fixture inclination and spacing, and secondary surgical site angulation limits for implanting substructure, such as anchors, into the patient's vital jawbone tissue. Upon completion of the preliminarily approved diagnostic prostheses 20 and 22, each of their baseplate portions 26 and 28, respectively, are separated from analogue portions 30 and 32, respectively, forming the artificial teeth and soft tissue.

With reference to FIG. 6, maxillary surgical stent 34 and mandibulary stent 36 are shown to be fabricated in association with their respective baseplates 26 and 28. More particularly, upon separation of baseplates 26 and 28 from their respective prostheses, each is trimmed to cover all necessary vestibular, palatal and buccal soft tissue previously demarcated by the surgeon upon which they will rest during implantation surgery. Preferably, baseplates 26 and 28 provide triposal support in their intraorally "as-mounted" position within the surgical area. With reference to the totally edentulous mandibulary situation, the anterior point of baseplate 28 provides tripodal support in combination with rear flanges 38 by nicking the soft stone tissue to approximate crestal bone height. A relatively short (i.e. approximately 2-3 mm) horizontal wire 40 is suitably secured into the perpendicular lingual wall 42 of base plate 28. While tripodal support is preferred it will be appreciated that other suitable methods of providing the requisite stability can also be utilized with the present invention.

In accordance with the principles of the present invention, each of the surgical cantilevered stent 34 and 36 shown is fabricated to include means for defining a predetermined spatial "reference" point approximating the "ideal" incisal edge and/or occlusal table height location from which the restorative dentist can fabricate a permanent prosthesis in proper registry with opposing dentition. Such means are shown to include one or more cantilevered supported guide wires 44 having a first end permanently fixed to baseplates 26 and 28. Guide wires 44 are preferably made of relatively rigid, yet workable, material such as 20 gauge stainless or titanium orthodontic wire. However, as will be appreciated, any suitable material providing the requisite standards of rigidity, sterility and precision can be used.

With continued reference to FIGS. 6 through 9, guide wires 44 are shown to be deformed (i.e. bent) beginning at their first end nearest their baseplate attachment locations to include a small pigtail 48 provided for secure retention in a suitable adhesive bonding layer, such as acrylic. Thereafter, a substantially right-angled bend is formed for defining an intermediate portion 50 which extends in a substantially vertical plane to approximate the "ideal" incisal edge or occlusal table height. At the preferred vertical length of intermediate portion 50, another substantially orthogonal bend is formed for defining a cantilevered wire portion 52 which extends in a substantially horizontal plane so as to project over and be substantially parallel to the crest of edentulous ridges 16 and 18.

At a second end of each support wire 44 the means for defining the predetermined spatial "reference" position is provided. According to the particular embodiment shown, such means include formation of a generally semi-circular centering loop 56 of a predetermined diameter. The diameter of each centering loop 56 is sufficiently large to permit the shank portion of all drill tools installed therein to move freely and without interference. Preferably, the center point of each semi-circular centering loop 56 is located slightly above and generally central to its underlying occlusal surface 58 for posterior teeth with the labial portion of each centering loop 56 being approximately lingual to the incisal edge 62 of anterior teeth 64. It is to be understood that guide wires 44 are to be located only in those areas of the jawbone where adequate bone is thought to be available. As noted, centering loops 56 preferably extend in a horizontal plane or are substantially parallel to the occlusal table. This preferred spatial positioning of cantilevered wire portions 52 and centering loops 56 is shown in FIGS. 7A and 7B for each of the diagnostic casts 12 and 14 with respect to the occlusal surface 58 and/or incisal edge 62 of diagnostic teeth analogues 30 and 32. The particular number and spacing between adjacent guide wires 44 is dependent on the specific edentulous condition being treated and is to be determined from clinical examination results.

Following precise bending of each guide wire 44, loops 56 are detachably secured to its corresponding underlying tooth analogue such as via sticky wax. This fabrication operation is utilized to ensure proper placement of centering loops 56 in the "ideal" locations during attachment of the first end of each guide wire 44 to baseplates 26 and 28. Thereafter, each baseplate 26 and 28 is roughed or scored and the first end of each guide wire 44 is secured thereto via application of a layer of cold curing powder and liquid acrylic resin. The acrylic resin is typically allowed to set in a heated water filled pressure pot at approximate 20 psi. However, it will be appreciated that any suitable bonding material or system can be readily used with the present invention. Once the pigtailed end 48 of guide wires 44 are securely bonded to baseplates 26, 28 then centering loops 56 are detached from its underlying teeth analogue.

With particular reference now to FIGS. 8 and 9, cantilevered surgical stents 34 and 36 are shown tripodally supported upon their respective master maxillary and mandibulary diagnostic casts 12 and 14 with respect to the modelled edentulous ridge surfaces 16 and 18. FIG. 9 illustrates the angulation of the screw exit locations for implanted anchors or fixtures 68 via elongated guide pin 70 which are shown threadly connected into internally threaded axial bores formed within fixtures 68. As is apparent, guide pins 70 illustrate the long axis angulation of implanted fixtures 68 within the bone of the edentulous ridge modelled herein. The predetermined spatial "reference" point is displaced from the edentulous ridges and, preferably, is defined as the center point of each centering loop 56 located in the horizontal plane of cantilevered wire portions 50 through which guide pins 70 extend. As such, cantilevered surgical stents 34 and 36 are designed to be applicable for use with any conventional cylindrical endosseous dental implant substructural devices and drilling tools commonly used.

According to a preferred surgical protocol, the surgeon is given cantilevered surgical stents 34 and 36 along with preliminary prostheses 20 and 22 for developing a better understanding of the overall prosthetic requirements and goals. In those situations where it is positively determined that adequate bone availability exists, a two guide wire system is provided. More specifically, a two guide wire system is shown in conjunction with maxillary stent 34 and includes a lower guide wire 72 and its cantilevered centering loop 74 that extends substantially parallel to and which is concentrically aligned below upper cantilevered centering loop 56 to define a "line of action" through which the surgeon will drill the implant bore into the bone. A first end of lower guide wire 72 is retained in baseplate 26 and its cantilevered centering loop 74 is positioned slightly above the edentulous ridge 16. Prior to reflection the mucous flap, a pilot drill is directed through the aligned center points of upper and lower cantilevered centering loops 56 and 74, respectively, for marking the bone underlying the soft tissue. Thereafter, lower guide wire 72 is removed from baseplate 26 prior to flap reflection to inhibit interference with the reflected flap. Such a two guide wire system can be incorporated into any cantilevered surgical stent of the present invention for limiting the surgeon to a rigid linear area within which adequate bone must be found (see FIG. 10). However, utilization of lower guide wire 72 is generally limited in most fixture placement locations due to typical uncertainty associated with bone availability.

It is anticipated that the majority of cantilevered surgical stents fabricated according to the present invention will be of the type having a majority of single guide wire systems as embodied in upper guide wires 44. As shown in FIG. 11, cantilevered semi-circular centering loop 56 of guide wire 44 permits the surgeon to loop apically in a conical area "C" with the apex defining the spatial reference point "R" which originates at the center of centering loop 56. Preferably, the long axis of the shank 76 for each of the various pilot, drill and tap tools must intersect the predetermined spatial "reference" point if the final permanent prothesis is to closely approximately the preliminary prothesis. Therefore, the present invention is directed to fabrication and utilization of surgical cantilevered stents which provide a three-dimensional view of screw exit locations relative to the cingulum or occlusal surfaces of the teeth analogues so as to permit the surgeon to apically look for available bone. As such, the cantilevered surgical stents are designed to permit the surgeon to controllably modify fixture angulation with respect to a spatial reference point "R" which is maintained independent of bone trajectory or angulation variability.

Another feature of the cantilevered surgical stents is that they permit the surgeon to reflex the soft gum tissue in virtually any direction. This is possible since the stent guide wires 44 are cantilevered from a position displaced from the surgical site. As such, the cantilevered surgical stents provide excellent access as well as superior visibility of the available bone region at the surgical site. Furthermore, in mandibulary totally edentulous patients, cantilevered surgical stent 36 provide even more convenience since its lingual vertical component 46 can retract a surgical flap which began as a buccal vestibular incision reflected lingually.

Utilization of a cantilevered surgical stent during the surgical implantation procedure is schematically shown in FIGS. 10 through 14. More particularly, FIG. 10 schematically illustrates shank portion 76 of an exemplary twist drill tool that is positioned and linearly constrained as it is guided through upper and lower guide wires 44 and 72, respectively, of the two guide wire system of the cantilevered surgical stent. Alternatively, FIG. 11 shows utilization of single guide wire 44 and its single upper centering loop 56 that is adapted to provide the surgeon with the ability to apically locate bone tissue. This apical ability (conical area "C") permits greater fixture implantation angulation without effecting the position of spatial reference point "R". Following initial drilling, bore 80 in the exposed bone structure is gradually widened using a series of sequentially wider spiral drill tools. Thereafter, the entrance of bore 80 is countersunk to better accommodate the head of fixtures 68. Next, final threading is provided via a titanium tap for making the drilled bore 80 congruent with fixtures 68 subsequently implanted therein. As shown in FIG. 12, the threaded titanium anchorage unit or fixture 68 is installed for osseointegration within tapped bore 80.

In accordance with conventional dental implantation surgical procedures, all drilling takes place at low rotational speeds with constant and profuse irrigation so as to minimize heat generation and mechanical trauma. Following threaded installation of fixture 68 into bore 80, a temporary screw cover 82 is threaded into the internal threaded bore 84 of fixture 68 to prevent bone growth over the fixture head during healing. Thereafter, the reflected mucosal flap 86 is carefully readapted for insulating full periosteal coverage of the anchor region. After the prescribed healing period, a second surgical procedure is provided for abutment connection. As shown in FIG. 14A and 14B, the surgeon uses a circular punch for excising mucosal tissue above each fixture 68. Thereafter, cover screw 82 is removed and abutment cylinders 88 are threadably connected to fixtures 68 via abutment screws 90.

Each of the fully edentulous cantilevered surgical stents 32 and 34 described thus far has incorporated single and two guide wire systems adapted for use with primary surgical sites which are defined to include those surgical sites where the clinically anticipated bone availability permits use of non-angulated abutments, similar to the type shown in FIG. 14B. However, if during the pre-surgical diagnostic evaluation it is determined or suspected that adequate bone volume may not be present, or the trajectory of the available one may require use of an angulated abutment, then secondary surgical sites can likewise be accommodated by the cantilevered surgical stents of the present invention. Moreover, a novel feature of the present invention is that screw exit locations for angulated abutments typically associated with secondary surgical sites, can be incorporated into the cantilevered surgical stent for use as a diagnostic tool and not as a "bail-out" measure for correcting improper angulation problems heretobefore associated with conventional stents.

Beginning with the "ideal" soft tissue location, an angulated abutment of any degree can have its drill site precisely located in three dimensional spatial terms. To more thoroughly discuss the accommodation of secondary surgical sites, reference should be made to FIGS. 15 through 18 wherein a partial edentulous maxillary diagnostic cast 100 is shown in association with its corresponding diagnostic prosthesis 102 and its cantilevered surgical stent 104. Cantilevered surgical stent 104 has a tripodal supporting baseplate 106 to which the first end of a primary site cantilevered guide wire 44 and a secondary site cantilevered guide wire 108 are securely retained. FIG. 15 also illustrates a vinyl polysiloxane registration 110 of the labial teeth analogues 112 of partial diagnostic prosthesis 102. As previously noted, the labial portion of centering loop 56 of guide wire 44 is preferably located lingual to the incisal edge 114 of the labial surface of tooth 112.

Figure 18:
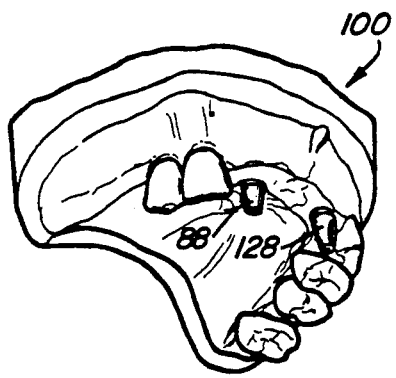
FIG. 18 is a perspective view, similar to FIG. 17, illustrating fixture placements for non-angulated and angulated abutments.

Secondary site guide wire 108 is configured similar to guide wire 44 and includes a vertically extending intermediate portion 116 and a cantilevered wire portion 118 extending substantially in a horizontal plane and which terminates in a semi-circular centering loop 120. Preferably centering loop 120 is formed to have a diametrical size that is similar to centering loop 56 of guide wire 44. More particularly, centering loop 120 of secondary site guide wire 108 is adapted to extend above and beyond the incisal edge of labial tooth 112. This spatial orientation is best shown in FIG. 17 and 18 which illustrate a comparison of the drilling inclinations for a primary surgical site, shown as axis 122, through centering loop 56, and a secondary surgical site, shown as axis 124, through centering loop 120. As is evident, the surgeon is able to apically look for available bone for fixture implantation within the secondary surgical site while maintaining a spacial reference point relative to a reference axis 126 from which the restorative dentist can fabricate the permanent prostheses. More particularly, axis 126 delineates the major axis of angulated abutment 128 and is shown in FIG. 17 to substantially align with the initial radial junction between wire portion 118 and centering loop 120. In fact, this axis orientation is designed to pass through the spatial point defining a primary surgical site for guide wire 108. As can be seen, secondary site guide wire 108 is basically a modification to primary site guide wire 44 which can be utilized as a diagnostic and surgical tool for utilization of angulated abutments 128 with corresponding accuracy.

Figure 19:
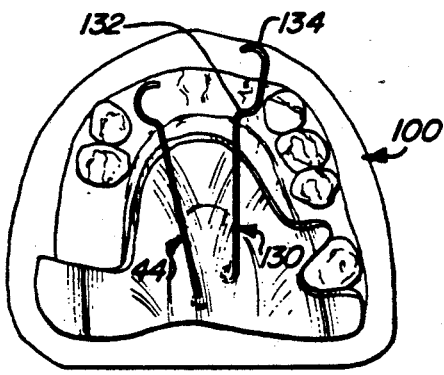
FIG. 19 is a plan view of the cantilevered surgical stent of FIG. 16 which has been modified to incorporate an alternative guide wire design for accommodating secondary surgical sites.

With reference now to FIG. 19, an alternative embodiment for a combination primary/secondary site guide wire 130 is shown that is adaptable for use with any of the previously described cantilevered surgical stents. More particularly, combination guide wire 130 provides the surgeon with a primary site centering loop 132 and a secondary site centering loop 134 for providing the surgeon with the ability to apically look for available bone in either a primary or secondary surgical site or anywhere linearly between the two reference points utilizing a single guide wire design. Therefore, the reference point associated with centering loop 132 defines the spatial position from which the restorative dentist works with either angulated or standard non-angulated abutments.

Figure 20:
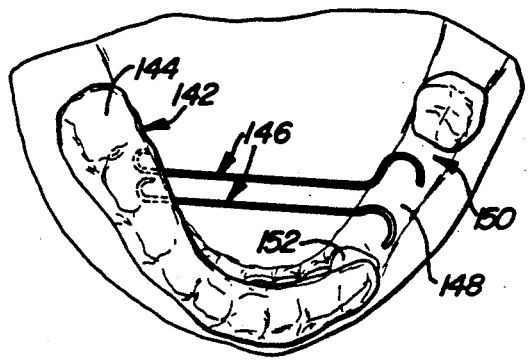
FIG. 20 is a view of another partially edentulous diagnostic cast illustrating the placement of a cantilevered surgical stent over existing teeth.

With reference to FIG. 20, another embodiment of a partially edentulous diagnostic cast 140 is shown having a cantilevered surgical stent 142 including a base portion 144 form which one or more guide wires 146 (two shown) extend over an occlusal space 148 in the edentulous ridge 150. Guide wires 146 can be of either the primary or secondary site type as previously disclosed herein. As such, cantilevered surgical stent 142 illustrates the ability to mount base 144 over existing teeth 152 utilizing the existing teeth for tripod stabilization.

Figure 21:
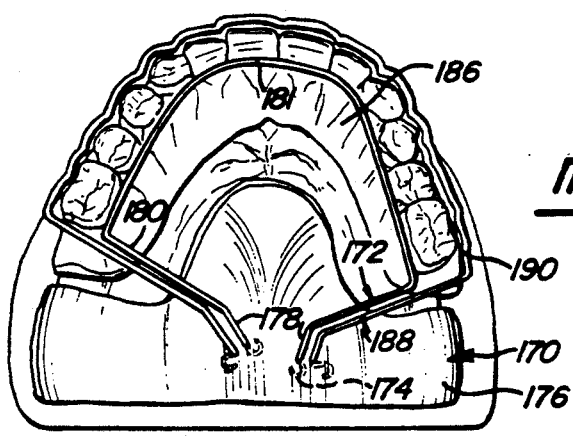
FIG. 21 is a top plan view of an alternative embodiment of a cantilevered surgical stent which can be used in fully edentulous situations.

Finally, FIG. 21 is a plan view of a cantilevered surgical stent 170 which can be used in virtually any fully or partially edentulous situation. More particularly, cantilevered surgical stent 170 includes unitary primary site guide wire 172 having each of its terminal pigtailed ends 174 mounted to baseplate 176. Primary site guide wire 172 includes a pair of spaced and vertically extending intermediate wire portions 178 which are sized to position and support a cantilevered centering portion 180 at its desired lingual limits and occlusal table heights. The cantilevered centering portion 180 includes a continuous band or chord 181 positioned at the most lingual extent near lingual cusps and the cingulums at occusal surfaces 182. While continuous chord 181 of centering portion 180 is shown to be generally arcuate, it likewise can be manipulated in various configurations to meet the needs of the specific fixture placements. With such a stent 170, the surgeon is then free to determine spacing and the specific number of fixture location based on actual evaluation of bone tissue following flap reflection while maintaining the ability to apically place the fixtures with respect to each corresponding reference point. As will be appreciated, following installation of stent 170 into the patient's mouth, the surgeon will drill each fixture bore 80 from a point slightly labial to the cantilevered chord at the peripheral positions of his choice. Therefore, each reference point is still maintained in the common horizontal plane defined by cantilevered centering portion 180. In addition, a secondary site guide wire 188 is provided labially of primary site guide wire 172 that is configured in a similar manner and which is applicable to accommodate angulated fixture inclination generally associated with secondary surgical sites. Secondary site guide wire 188 includes cantilevered centering portion 190 that is supported from baseplate 176 so as to extend above and beyond prosthesis 186. The location of cantilevered portion 190 of secondary guide wire 188 defines the maximum fixture inclination limit up to which currently available angulated abutments can be used for proper prosthodontic results. The surgeon centers the drill tool anywhere between adjacent cantilevered centering portions 181 and 190 for apically drilling the anchor bore.

The foregoing discussion discloses and merely describes exemplary embodiments of the present invention. One skilled in the art will recognize from such discussion, and from the accompanying drawings and claims, that various changes, modifications and variations can be made therein without departing from the true spirit and fair scope of the invention as defined in the following claims. For example, while the means for defining a predetermined spacial reference point are disclosed to include semi-circular centering loops, it will be appreciated that other end configurations for the cantilevered wire portion would also be in the fair scope of the present invention.

What is claimed is:

1. A cantilevered surgical stent which is placed in a patient's mouth for permitting a surgeon to implant one of more endosseous dental implant fixtures in a desired orientation with respect to an edentulous ridge section of the patient's jawbone, said surgical stent comprising:
   a base member positioned within the patient's mouth; and
   guide means cantilevered from said base member for spatially orienting said dental implant fixture with respect to a predetermined reference point displaced from said edentulous ridge including a guide wire having a first portion fixedly coupled to said base member, and a second portion adjacent said first portion which is cantilevered from said base member, said second portion including centering means for spatially locating said predetermined reference point with respect to said edentulous ridge section such that said predetermined referenced point defines the apex of a conical area having its base located at said edentulous ridge section, wherein the surgeon is able to apically select a desired drill trajectory with respect to said predetermined reference point for implantation of said dental implant fixture into said edentulous ridge section, said predetermined reference point being spatially positioned for approximating a desired incisal edge or occlusal table height from which a prosthesis can be fabricated that is in proper registry with opposing dentition.

2. The cantilevered surgical stent of claim 1 wherein said centering means is positioned remotely from said base member for spatially locating said predetermined reference point slightly above and generally central to an underlying occlusal surface or incisal edge associated with said prosthesis.

3. The cantilevered surgical stent of claim 2 wherein said cantilevered second portion and said centering means extend in a substantially horizontal plane which is displaced from and is substantially parallel to said edentulous ridge section of said jawbone.

4. The cantilevered surgical stent of claim 3 wherein said centering means includes a generally semi-circular centering loop formed in said second portion of said guide wire, and wherein a center point of said semi-circular centering loop defines said predetermined spatial reference point and which is spatially positioned slightly above and generally central to said underlying occlusal surface for posterior portions of said edentulous ridge section, and said semi-circular centering loop having its labial portion spatially located approximately lingual to said incisal edge of an anterior portion of said edentulous ridge section, whereby such spatial orientation of said semi-circular centering loop defines a primary surgical site with respect to said edentulous ridge section from which apical implant trajectory is permitted.

5. The cantilevered surgical stent of claim 4 wherein said centering means further comprises a second generally semi-circular centering loop formed adjacent said first centering loop for defining a second predetermined reference point spatially displaced from said first reference point, said second predetermined reference point is displaced from said first reference point for defining a secondary surgical site with respect to said edentulous ridge section, said second semi-circular centering loop being co planar with and extending beyond said first semi-circular centering loop so as to extend slightly labially of said edentulous ridge section such that the surgeon is able to apically look for available bone for implantation of said dental fixture within said secondary surgical site while said first centering loop acts to maintain spatial orientation of said first reference point from which said prosthesis can be fabricated.

6. The cantilevered surgical stent of claim 3 wherein said base member is configured to be tripodally supported within said patient's mouth so as to be located remotely from said cantilevered centering means.

7. The cantilevered surgical stent of claim 3 wherein said first portion of said guide wire comprises a pair of spaced wire portions fixed to said base member and said centering means comprises a continuous chordal wire portion interconnecting said pair of spaced wire portions, said chordal wire portion being cantilevered relative to said base member and configured to follow a path approximating said desired lingual and occlusal surfaces of said edentulous ridge section, whereby the surgeon is permitted to locate said predetermined reference point from a point slightly labial to said cantilevered chordal wire portion for defining a primary surgical site.

8. The cantilevered surgical stent of claim 7 further including a second guide wire having a second pair of spaced wire portions fixedly coupled to said base member and a second cantilevered chordal wire portion that is spatially located labially relative to said first chordal wire portion of said first guide wire for defining a second reference point associated with secondary surgical sites, whereby the surgeon is permitted to center a drill tool anywhere between said adjacent chordal wire portions of said first and second guide wires for apically drilling into said edentulous ridge section while maintaining spatial orientation of said first reference point from which said prosthesis can be fabricated.

9. A method for fabricating a cantilevered surgical stent to be placed in a patient's mouth for permitting a surgeon to implant one or more endosseous dental implant fixtures in a desired orientation with respect to an edentulous ridge section of the patient's jawbone, said method comprising the steps of:
   forming a reproduction via diagnostic casts of the patient's edentulous ridge section;
   predicting the bone availability within the edentulous ridge section for dental implant placement therein;
   fabricating a preliminary diagnostic prosthesis having proper occlusal alignment with opposing dentition;

fabricating the cantilevered surgical stent to include base means for direct placement in the patient's mouth and cantilevered guide means which extend from said base means for defining a predetermined spatial reference point with respect to said preliminary diagnostic prosthesis and its underlying edentulous ridge, said predetermined reference point being spatially located remotely from said base means for approximating a preferred incisal edge or occlusal table height location for the implanted fixtures whereby fabrication of a permanent prosthesis having proper registration with opposing dentition is permitted with respect to said predetermined reference point.

10. The method of claim 9 wherein said step of fabricating the cantilevered surgical stent includes forming said base means from a portion of said preliminary diagnostic prosthesis, and forming said cantilevered guide means to include a guide wire having a first portion fixedly coupled to said base means and a second portion adjacent said first portion which is cantilevered from said base means, said second portion including centering means for spatially locating said predetermined reference point relative to the edentulous ridge for approximating said preferred incisal edge or occlusal table height location with said predetermined reference point being spatially displaced from said edentulous ridge section.

11. The method of claim 10 wherein said cantilevered second portion and said centering means are formed to extend in a substantially horizontal plane which is displaced from and is substantially parallel to said edentulous ridge.

12. The method of claim 11 wherein said centering means includes a generally semi-circular centering loop formed in said second portion of said guide wire, and wherein a center point of said semi-circular centering loop defines said predetermined reference point which is spatially positioned slightly above and generally central to said underlying occlusal surface for posterior portions of said edentulous ridge section, and said semi-circular centering loop having its labial portion spatially located approximately lingual to said incisal edge of an anterior portion of said edentulous ridge section, whereby such spatial orientation of said semi-circular centering loop defines a primary surgical site with respect to said edentulous ridge section from which apical implant trajectory is permitted.

13. The method of claim 12 wherein said first portion of said guide wire comprises a pair of spaced wire portions fixed to said base member means and said centering means comprises a continuous chordal wire portion interconnecting said pair of spaced wire portions, said chordal wire portion being cantilevered relative to said base means and configured to follow a path approximating said desired lingual and occlusal surfaces of said edentulous ridge section, whereby the surgeon is permitted to spatially locate said predetermined reference point from a point slightly labial to said cantilevered chordal wire portion for defining a primary surgical site.

14. The method of claim 13 further comprising the step of fixing a second guide wire to said base means, said second guide wire having a second pair of spaced wire portions fixedly coupled to said base means and a second cantilevered chordal wire portion that is spatially located labially relative to said first chordal wire portion of said first guide wire for defining a second reference point associated with secondary surgical sites, whereby the surgeon is permitted to center a drill tool anywhere between said adjacent chordal wire portions of said first and second guide wires for apically drilling into said edentulous ridge section while maintaining spatial orientation of said first reference point from which said prosthesis can be fabricated.

15. A method for spatially orienting an endosseous dental implant fixture with respect to a predetermined reference point during dental implant surgery, said method comprising the steps of:
   placing a cantilevered surgical stent in the patient's mouth so as to position a base member of said cantilevered surgical stent with respect to an edentulous ridge section of the patient's jawbone, said cantilevered surgical stent having guide means cantilevered from said base member and adapted for defining the predetermined spatial reference point with respect to said edentulous ridge;
   locating a drill tool relative to said cantilevered guide means such that a shank portion of said drill tool intersects the predetermined spatial reference point, said predetermined reference point defines an apex of a conical area having its base located at said edentulous ridge;
   apically selecting a drill trajectory into said edentulous ridge section with respect to said predetermined spatial reference point;
   drilling a bore into said edentulous ridge section of the patient's jawbone along said selected drill trajectory; and
   implanting the endosseous dental implant fixture within said bore whereby said cantilevered surgical stent permits fixture angulation in said edentulous ridge while spatially maintain said predetermined reference point.

* * * * *